United States Patent
Koch et al.

(10) Patent No.: US 7,041,776 B2
(45) Date of Patent: May 9, 2006

(54) PROCESS FOR THE PRODUCTION OF POLYISOCYANATES OF THE DIPHENYLMETHANE SERIES BY PHOSGENATION OF NON-NEUTRALIZED POLYAMINE OF THE DIPHENYLMETHANE SERIES

(75) Inventors: Daniel Koch, Duisburg (DE); Hans-Georg Pirkl, Leverkusen (DE); Torsten Hagen, Essen (DE); Stefan Wershofen, Mönchengladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 10 days.

(21) Appl. No.: 10/672,440

(22) Filed: Sep. 26, 2003

(65) Prior Publication Data

US 2004/0092701 A1    May 13, 2004

(30) Foreign Application Priority Data

Sep. 30, 2002  (DE) ............................... 102 45 703

(51) Int. Cl.
*C08G 12/06*  (2006.01)

(52) U.S. Cl. ...................... 528/269; 528/266; 560/347; 560/338; 560/359; 564/330; 564/331; 564/333

(58) Field of Classification Search ................ 528/269, 528/266; 560/347, 338, 359; 564/330, 331, 564/333
See application file for complete search history.

(56) References Cited

U.S. PATENT DOCUMENTS 4,597,909 A * 7/1986 Keggenhoff et al. ........ 560/347
5,310,769 A * 5/1994 Konig et al. ................ 521/163

FOREIGN PATENT DOCUMENTS

| DE | 24 04 775 | 8/1975 |
|---|---|---|
| GB | 1 203 546 | 8/1970 |
| WO | 01/74755 | 10/2001 |

OTHER PUBLICATIONS

Chem. Soc. Rev. 3(2), 209 (month unavailable) 1974, pp. 209-230, H. J. Twitchett, "Chemistry of the Production of Organic Isocyanates".

Kirk-Othmer Encycl. Chem. Technol., $3^{rd}$ ed. New York, 2, (month unavailable) 1978, pp. 338-348, William M. Moore, "Methylenedianiline".

* cited by examiner

*Primary Examiner*—Duc Truong
(74) *Attorney, Agent, or Firm*—Joseph C. Gil; N. Denise Brown

(57) ABSTRACT

The invention relates to a method of producing polyisocyanates of the diphenylmethane series including the steps of
a) reacting aniline and formaldehyde in the presence of HCl to provide a product mixture containing polyamines of the diphenylmethane series, HCl, aniline and water;
b) removing excess aniline and water by distillation to provide a product mixture comprising polyamines of the diphenylmethane series, HCl, no more than 10 wt. % aniline based on the polyamines, and no more than 5 wt. % water based on the polyamines; and
c) phosgenating the product mixture in (b).

9 Claims, No Drawings

PROCESS FOR THE PRODUCTION OF POLYISOCYANATES OF THE DIPHENYLMETHANE SERIES BY PHOSGENATION OF NON-NEUTRALIZED POLYAMINE OF THE DIPHENYLMETHANE SERIES

CROSS REFERENCE TO RELATED PATENT APPLICATION

The present patent application claims the right of priority under 35 U.S.C. §119 (a)–(d) of German Patent Application No. 102 45 703.4, filed Sep. 30, 2002.

FIELD OF THE INVENTION

The invention relates to a process for the production of polyisocyanates of the diphenylmethane series, which are obtained by reacting the corresponding polyamines of the diphenylmethane series with phosgene.

BACKGROUND OF THE INVENTION

Polyisocyanates of the diphenylmethane series are generally understood to include isocyanates and mixtures of isocyanates of the following type:

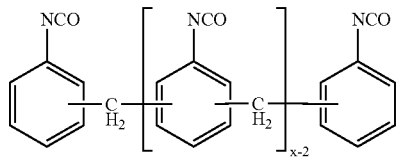

x = 2 to n

Similarly, polyamines of the diphenylmethane series are generally understood to include compounds and mixtures of compounds of the following type:

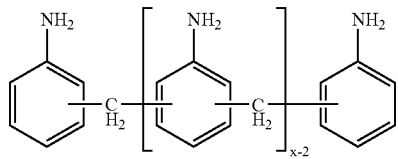

x = 2 to n

The industrial production of isocyanates by the reaction of amines with phosgene in solvents is known and is described in detail in the literature (Ullmanns Enzyklopädie der technischen Chemie, 4$^{th}$ edition, volume 13, pages 347–357, Verlag Chemie GmbH, Weinheim, 1977). Based on this process, a mixture of polyisocyanates is produced which is used as the polyisocyanate component in the production of polyurethane foams and other polyurethane plastics produced by polyaddition processes.

The continuous, non-continuous or semi-continuous production of polyamines of the diphenylmethane series, also referred to below as MDA, is described in numerous patents and publications. The production conventionally takes place by reacting aniline and formaldehyde in the presence of acidic catalysts. HCl is conventionally used as the acidic catalyst. According to the prior art, the acidic catalyst is neutralised at the end of the process before the final reprocessing steps (such as e.g. the removal of excess aniline by distillation) by adding a base, and is thus consumed.

The main products of the acid-catalysed reaction of aniline and formaldehyde are the diamine 4,4'-MDA, its positional isomers 2,4'-MDA and 2,2'-MDA and higher homologues of polyamines of the diphenylmethane series. The polyisocyanates of the diphenylmethane series, referred to below as MDI, are produced by phosgenation of the corresponding polyamines. The polyisocyanates of the diphenylmethane series produced in this way contain the various isocyanate isomers and their higher homologues in the same composition as the polyamines from which they were produced. The controlling variable for influencing the isomer distribution is the quantity of acidic catalyst used in the process during the acid-catalysed reaction of aniline and formaldehyde. To be able to produce MDI with the desired isomer distribution, therefore, it is sometimes necessary to use considerable quantities of acidic catalyst and correspondingly considerable quantities of base for neutralising the acidic catalyst. This further leads to quite large quantities of salt-containing waste water streams and, correspondingly, high costs for reprocessing and disposal.

For some time, it has been the goal of numerous trials and studies described in the literature to find processes to avoid or alleviate this problem. Thus, for example, WO-A1-0174755 describes the production of polyamines of the diphenylmethane series in the presence of heterogeneous catalysts, which take on the role of the acidic catalyst. In contrast to the homogeneous catalysts conventionally used, this type of catalyst can be separated from the reaction mixture by simple means and does not then have to be neutralised before being reprocessed. However, a disadvantage of this process is that the acidic solid deactivates over time and that the range of products obtainable using these catalysts is limited. EP-A1-1167343 describes MDA production according to the prior art, extended by an additional separation of the 2,4'-MDA and 2,2'-MDA isomers, and also their reaction with formaldehyde and recycling of this mixture to the beginning of the process. The recycled isomers are thus preferentially converted to higher-molecular-weight MDA components. This means that the close association between catalyst use and formation of 2,4'- and 2,2'-MDA is moderated by introducing another controlling variable. A disadvantage of this process, however, is that the conversion of the recycled isomers to higher MDA homologues can have a negative effect on the product properties of the MDI produced by subsequent phosgenation, and that additional outlay on apparatus is needed for distillation for the separation of isomers.

The object of the present invention was therefore to provide a process for the production of polyisocyanates of the diphenylmethane series, in which the consumption of acidic catalyst and correspondingly of base for neutralising the acidic catalyst at the MDA stage can be reduced or avoided.

SUMMARY OF THE INVENTION

The present invention is directed to a method of producing polyisocyanates of the diphenylmethane series including the steps of
  a) reacting aniline and formaldehyde in the presence of HCl to provide a product mixture containing polyamines of the diphenylmethane series, HCl, aniline and water;

b) removing excess aniline and water by distillation to provide a product mixture comprising polyamines of the diphenylmethane series, HCl, no more than 10 wt. % aniline based on the polyamines, and no more than 5 wt. % water based on the polyamines; and c) phosgenating the product mixture in (b).

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

As used herein, the term "largely removed" is meant to indicate that a material can be present in an incidental amount, which does not effect desired properties. In other words, the material is intentionally removed from an indicated composition, but may be present at minor or inconsequential levels.

The object of the present invention is achieved by a process for the production of polyisocyanates of the diphenylmethane series, in which a) aniline and formaldehyde are reacted in the presence of HCl to give a product mixture containing polyamines of the diphenylmethane series, HCl, aniline and water, and then b) excess aniline and water are removed by distillation, a product mixture containing polyamines of the diphenylmethane series, HCl and aniline with a content of no more than 10 wt. %, based on the polyamines, and water with a content of no more than 5 wt. %, based on the polyamines, being obtained, and then c) the product mixture, containing polyamines of the diphenylmethane series, HCl and aniline with a content of no more than 10 wt. %, based on the polyamines, and water with a content of no more than 5 wt. %, based on the polyamines, is phosgenated.

The process can be conducted continuously, non-continuously or semi-continuously. Polyisocyanates of the diphenylmethane series can be produced by the process without neutralising the acidic catalyst HCl at the MDA production stage.

The polyamine or mixture of polyamines of the diphenylmethane series produced according to the process in step a) is obtained by condensation of aniline and formaldehyde in the presence of the acidic catalyst as described for example, by H. J. Twitchett, Chem. Soc. Rev. 3(2), 209 (1974), M. V. Moore in: Kirk-Othmer Encycl. Chem. Technol., 3$^{rd}$ ed., New York, 2, 338–348 (1978). The sequence of addition is not particularly import to the method according to the invention, hence aniline and formaldehyde can be mixed first in the absence of HCl and HCl is then added, or, alternatively, a mixture of aniline and HCl can be reacted with formaldehyde.

Suitable mixtures of polyamines of the diphenylmethane series are conventionally obtained by condensation of aniline and formaldehyde in a molar ratio of 20:1 to 1.6:1, and in some cases 10:1 to 1.8:1, and a molar ratio of aniline and HCl of 50:1 to 1:1, and in some cases 20:1 to 2:1.

Formaldehyde is conventionally used as an aqueous solution. However, other suitable compounds providing methylene groups can also be used. Suitable compounds that provide methylene groups include, but are not limited to polyoxymethylene glycol, para-formaldehyde or trioxane.

Suitable acidic catalysts, non-limiting examples of which include strong organic acids and particularly inorganic acids, are typically used as acidic catalysts for MDA production. As a non-limiting example, for the process according to the invention, HCl is a suitable acidic catalyst, typically in the form of an aqueous solution.

In a particular embodiment of the present method, aniline and HCl are first combined to form a mixture. In a further step, the mixture is mixed with formaldehyde in a suitable manner at a temperature of from 20° C. to 100° C., and in some cases from 30° C. to 70° C. Optionally, after dissipation of heat, the mixture is then subjected to a preliminary reaction in suitable residence-time apparatus. The preliminary reaction takes place at a temperatures of from 20° C. to 100° C., and in some cases at a temperature of from 30° C. to 80° C. Following the mixing and preliminary reaction, the temperature of the reaction mixture is brought, stepwise or continuously and optionally under excess pressure, to from 100° C. to 250° C., in some cases to from 100° C. to 180° C., and in other cases to from 100° C. to 160° C.

In another embodiment of the present method, it is also possible to mix aniline and formaldehyde first in the absence of HCl at a temperature of from 5° C. to 130° C., in some cases from 40° C. to 110° C., an in other cases from 60° C. to 100° C., and to react them in as described above. The reaction leads to the formation of condensation products of aniline and formaldehyde (referred to as an aminal).

Following aminal formation, water present in the reaction mixture can be removed by phase separation or other appropriate process steps, a non-limiting example being by distillation. The condensation product is then mixed with HCl in a suitable manner in another process step and subjected to a preliminary reaction in a residence-time apparatus at from 20° C. to 100° C., and in some cases at from 30° C. to 80° C. The temperature of the reaction mixture is then brought, stepwise or continuously and optionally under excess pressure, to from 100° C. to 250° C., in some cases to from 100° C. to 180° C., and in other cases from 100° C. to 160° C.

The reaction of aniline and formaldehyde in the presence of HCl to give polyamines of the diphenylmethane series can take place in the presence of other substances, which may include, but are not limited to solvents, salts, organic and inorganic acids.

In addition to the desired MDA, the product mixture obtained in step a) also contains aniline, which is used in excess, water, HCl as a catalyst and optionally other substances that were added to the process. Before converting the mixture to the corresponding MDI by phosgenation, the excess aniline and the water must first be largely removed from the mixture. Aniline contents of no more than 10 wt. %, in some cases no more than 2 wt. %, and in other cases no more than 0.2 wt. %, based on the polyamines, and water contents of no more than 5 wt. %, in some cases no more than 1 wt. %, and in other cases no more than 0.1 wt. %, based on the polyamines, must be established in the process.

Aniline has to be largely removed from the product mixture obtained in step a) before phosgenation because aniline would be converted to phenyl isocyanate during the phosgenation. Phenyl isocyanate is undesirable in MDI, however, owing to its chain-terminating monofunctionality.

The removal of water is necessary because water present during phosgenation would react both with phosgene and with the products and intermediate products of the phosgenation, and a reduced yield and undesirable by-products in the MDI would therefore result.

The removal of aniline in step b) can be achieved by distillation, although the aniline is present at least partly in its protonated form through reaction with HCl. Water, which is present in the reaction mixture anyway, also has to be removed, and is typically used as an entrainer for the removal of the aniline. However, it is also possible to use other organic or inorganic entrainers. For example, it is possible to use as an entrainer, the solvent that is also used in the phosgenation.

The separation of aniline and water advantageously takes place such that the acidic reaction mixture from the aniline/formaldehyde condensation is fed into a distillation column. The mixture of aniline and water and optionally additional entrainer is removed as a low-boiling fraction at the head of the column. The aniline can optionally be recycled into the MDA production after reprocessing, by phase separation as a non-limiting example. The product mixture remaining at the bottom is largely free of aniline and water and contains aniline at a level of no more than 10.0 wt. %, based on the polyamines, and water at a level of no more than 5.0 wt. %, based on the polyamines. To establish the low aniline contents desired, an additional feed of water and/or other entrainer may be necessary. This can take place, for example, by feeding an appropriate quantity of water and/or solvent into the material flowing into the distillation stage. However, it is also possible to introduce the required quantity of water or solvent into the distillation stage in vapour form, and thus to input the energy needed for the distillation at the same time.

In an embodiment of the invention, it is also possible to perform the separation of aniline and water in more than one step, as a non-limiting example, in two steps. The separation can involve separating off aniline by distillation with water as the entrainer and, in a distillation step, separating off water using another entrainer.

In this embodiment, an aniline level of no more than 10 wt. %, in some cases no more than 2 wt. %, and in other cases no more than 0.2 wt. %, based on the polyamines, and a water level of no more than 5 wt. %, in some cases no more than 1 wt. %, and in other cases no more than 0.1 wt. %, based on the polyamines, must be established.

The product mixture obtained according to this embodiment contains polyamines of the diphenylmethane series and HCl as the main components, together with possible residual contents of aniline and water, with some of the polyamines and possibly aniline being present in protonated form. Nevertheless, this product mixture can then be reacted with phosgene in an inert organic solvent to form the corresponding isocyanates. The molar ratio of polyamine to phosgene is usefully calculated such that 1 to 10 moles, and in some cases 1.2 to 6 moles, of phosgene are used per mole of amine function in the polyamine. Chlorinated, aromatic hydrocarbons, such as e.g. monochlorobenzene, dichlorobenzenes, trichlorobenzenes, the corresponding (optionally chlorinated) toluenes and xylenes and also chloroethylbenzene have proved suitable as inert solvents for the phosgenation step. Monochlorobenzene, dichlorobenzene or mixtures of these chlorobenzenes are particularly used as inert organic solvents. The quantity of solvent is typically calculated such that the reaction mixture has an MDI content of from 2 to 50 wt. %, and in some cases from 5 to 30 wt. %, based on the total weight of the reaction mixture. On completion of the reaction of amine and phosgene, excess phosgene, inert organic solvents and HCl are separated from the reaction mixture. The separated HCl in this cases is made up of the HCl formed during the phosgenation of MDA with phosgene and the HCl used as catalyst for the reaction of aniline with formaldehyde to form MDA. MDI is obtained as the product, which can be subjected to further reprocessing steps.

The process according to the invention has the advantage that it can dispense with the use of a base such as NaOH for neutralising the HCl used. As a result, salt-containing waste water streams and the associated reprocessing and disposal costs are avoided. The HCl used as catalyst in the condensation of aniline and formaldehyde is recovered as a useful substance during the phosgenation and can be recycled into the MDA process after suitable reprocessing. In addition, it is possible to dispense with a neutralisation and washing step in the MDA process.

The invention is further illustrated but is not intended to be limited by the following examples in which all parts and percentages are by weight unless otherwise specified.

EXAMPLES 884 g of aniline and 486 g of a 32% aqueous formaldehyde solution were added dropwise, at the same time, to 513 g of aniline at 80° C. within 20 min. After the addition, stirring was continued for 10 min and a phase separation was then performed at 70–80° C. A quantity of 356 g of the organic phase was brought to a temperature of 35° C. and then the remaining organic phase and 427 g of a 32% aqueous hydrochloric acid were added at this temperature within 30 minutes. On completion of the addition and after a further 30-minute period of stirring at this temperature, the mixture was heated to 60° C. for 10 min and kept at this temperature for 30 min. It was then heated to reflux temperature within 30 min and stirred under reflux for 10 h.

1177 g of the acidic condensation mixture produced was transferred to a non-continuous distillation apparatus and brought to an aniline content in the bottom of less than 0.1 wt. %, based on polyamine, by blowing water vapour into the bottom of the column. Chlorobenzene was continuously added to the largely aniline-free bottom mixture, still containing water and HCl, in a second distillation apparatus, and kept at boiling point until the water content in the bottom fell to less than 0.1 wt. %, based on polyamine. The mixture of chlorobenzene and water condensing at the head can be separated by phase separation to return the chlorobenzene to the distillation.

The largely aniline- and water-free, acidic rearrangement mixture from the aniline/formaldehyde condensation now present as a suspension in chlorobenzene was removed from the distillation apparatus. Chlorobenzene was then added and a polyamine content of 16 wt. %, based on the suspension, was established.

300 g of this suspension was heated to 55° C. and rapidly added, with vigorous stirring, to a solution of 105 g of phosgene in 310 ml of chlorobenzene, controlled at a temperature of 0° C. The resulting reaction mixture was heated to 100° C. within 45 min while phosgene was passed through, and then heated to reflux temperature for 10 min. After a further 10 min at this temperature, the chlorobenzene was distilled off under reduced pressure to a bottom temperature of 100° C. The clear crude isocyanate was then heated in a distillation apparatus under a pressure of 4–6 mbar by a heating bath heated to 260° C. until the beginning of product transition, and then cooled to ambient temperature within 5 min.

The MDI obtained had an NCO content of 32.5 wt. % based on MDI.

The present invention has been described with reference to specific details of particular embodiments thereof. It is not intended that such details be regarded as limitations upon the scope of the invention except insofar as and to the extent that they are included in the accompanying claims.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of producing polyisocyanates of the diphenylmethane series comprising:
   a) reacting aniline and formaldehyde in the presence of HCl to provide a product mixture containing polyamines of the diphenylmethane series, HCl, aniline and water;
   b) removing excess aniline and water by distillation to provide a product mixture comprising polyamines of the diphenylmethane series, HCl, no more than 10 wt. % aniline based on the polyamines, and no more than 5 wt. % water based on the polyamines; and
   c) phosgenating the product mixture from (b) which comprises polyamines of the diphenylmethane series, HCl, no more than 10 wt. % aniline based on the polyamines, and no more than 5 wt% water based on the polyamines;

wherein the acidic HCl catalyst is not neutralized.

2. The method according to claim 1, wherein the distillation is performed in the presence of an entrainer.

3. The method according to claim 1, wherein the distillation is performed by a method comprising removing aniline by distillation in the presence of water as entrainer; and removing water by distillation.

4. The method according to claim 1, wherein, the product mixture in (b) comprises no more than 2 wt. % aniline based on the polyamines, and no more than 1 wt. % water with based on the polyamines.

5. The method according to claim 2, wherein, the product mixture in (b) comprises no more than 2 wt. % aniline based on the polyamines, and no more than 1 wt. % water with based on the polyamines.

6. The method according to claim 3, wherein, the product mixture in (b) comprises no more than 2 wt. % aniline based on the polyamines, and no more than 1 wt. % water based on the polyamines.

7. The method according to claim 1, wherein the product mixture in (b) comprises no more than 0.2 wt. % aniline based on the polyamines, and no more than 0.1 wt. % water based on the polyamines.

8. The method according to claim 2, wherein the product mixture in (b) comprises no more than 0.2 wt. % aniline based on the polyamines, and no more than 0.1 wt. % water based on the polyamines.

9. The method according to claim 3, wherein the product mixture in (b) comprises no more than 0.2 wt. % aniline based on the polyamines, and no more than 0.1 wt. % water based on the polyamines.

* * * * *